(12) United States Patent
Hoghooghi et al.

(10) Patent No.: US 12,390,548 B2
(45) Date of Patent: Aug. 19, 2025

(54) SYSTEM AND METHOD FOR PROTECTING A WORKSPACE FROM AIRBORNE CONTAMINANTS

(71) Applicants: Mehrdad Michael Hoghooghi, Ellicott City, MD (US); Hamidreza Abbass-Movahedi, Hollister, CA (US); Parsa Amir-Mansour Hoghooghi, Ellicott City, MD (US); Hunyeh Neda Hoghooghi, Ellicott City, MD (US)

(72) Inventors: Mehrdad Michael Hoghooghi, Ellicott City, MD (US); Hamidreza Abbass-Movahedi, Hollister, CA (US); Parsa Amir-Mansour Hoghooghi, Ellicott City, MD (US); Hunyeh Neda Hoghooghi, Ellicott City, MD (US)

( * ) Notice: Subject to any disclaimer, the term of this patent is extended or adjusted under 35 U.S.C. 154(b) by 1038 days.

(21) Appl. No.: 17/302,874

(22) Filed: May 14, 2021

(65) Prior Publication Data

US 2021/0353818 A1   Nov. 18, 2021

Related U.S. Application Data

(60) Provisional application No. 63/025,103, filed on May 14, 2020.

(51) Int. Cl.
*A61L 9/20* (2006.01)
*A61L 9/14* (2006.01)
(Continued)

(52) U.S. Cl.
CPC ............... *A61L 9/20* (2013.01); *A61L 9/14* (2013.01); *B01D 46/0028* (2013.01);
(Continued)

(58) Field of Classification Search
CPC ........................................................ A61L 9/20
See application file for complete search history.

(56) References Cited

U.S. PATENT DOCUMENTS 5,061,296 A * 10/1991 Sengpiel ................... A61L 9/16
96/24
7,655,080 B2   2/2010 Ting
(Continued)

FOREIGN PATENT DOCUMENTS

CN           20400637      12/2014
JP          4871868 B2     11/2011
(Continued)

*Primary Examiner* — Donald R Spamer
(74) *Attorney, Agent, or Firm* — Sagacity Legal PLLC (57) ABSTRACT

A system for protecting a workspace from airborne contaminants comprises at least one sensing capturing unit, an air transmission unit, an air capturing unit, and a processor. The processor is configured to receive a sensing data associated with the workspace from the at least one sensing capturing unit and determine presence of at least one source of transmission of the airborne contaminants. The processor is further configured to configure a capture zone within the workspace based on the determined at least one source of transmission of the airborne contaminants. The processor is configured to control the air transmission unit to direct a unidirectional flow of air over the configured capture zone, thereby directing movement of the airborne contaminants in the capture zone and further to control the air capturing unit to capture the unidirectional flow of air, along with the airborne contaminants, directed from the air transmission unit.

9 Claims, 6 Drawing Sheets

(51) Int. Cl.
  *B01D 46/00*  (2022.01)
  *B01D 46/44*  (2006.01)
  *B01D 46/46*  (2006.01)
  *F24F 8/10*  (2021.01)
  *F24F 11/79*  (2018.01)
  *F24F 110/64*  (2018.01)

(52) U.S. Cl.
  CPC ....... *B01D 46/0086* (2013.01); *B01D 46/448* (2013.01); *B01D 46/46* (2013.01); *F24F 8/10* (2021.01); *F24F 11/79* (2018.01); *A61L 2209/111* (2013.01); *A61L 2209/14* (2013.01); *B01D 2279/50* (2013.01); *F24F 2110/64* (2018.01)

(56) References Cited

U.S. PATENT DOCUMENTS

| | | | |
|---|---|---|---|
| 7,838,532 B2 | 11/2010 | Surber et al. | |
| 8,066,802 B2 | 11/2011 | Kristensson et al. | |
| 8,565,892 B2 | 10/2013 | Nayfach-Battilana | |
| 9,010,019 B2 | 4/2015 | Mittlemark | |
| 9,050,382 B2 | 6/2015 | Carr | |
| 9,150,631 B2 | 10/2015 | Super et al. | |
| 9,291,549 B2 | 3/2016 | Schwoebel et al. | |
| 9,522,396 B2 | 12/2016 | Bachelet et al. | |
| 9,700,642 B2 | 7/2017 | Neister | |
| 10,724,935 B2 | 7/2020 | Lucas et al. | |
| 2003/0127603 A1 | 7/2003 | Horowitz et al. | |
| 2013/0157283 A1 | 6/2013 | Yung et al. | |
| 2014/0100136 A1 | 4/2014 | Clarizia et al. | |
| 2014/0271347 A1* | 9/2014 | Park | A61L 2/22 422/3 |
| 2019/0134434 A1* | 5/2019 | Schuller | A62B 7/10 |
| 2019/0234645 A1* | 8/2019 | Haar | F24F 7/003 |
| 2019/0366263 A1 | 12/2019 | Zhu | |
| 2020/0042861 A1 | 2/2020 | Park | |
| 2020/0182495 A1* | 6/2020 | Park | F24F 8/10 |

FOREIGN PATENT DOCUMENTS

| | | |
|---|---|---|
| WO | 199900043362 A1 | 9/1999 |
| WO | 2020149285 A1 | 7/2020 |

\* cited by examiner

| DEVICE 1 | DEVICE 2 | DEVICE N | OPERATING PROFILE | POSITIONAL INFORMATION OF CAPTURE ZONE | OPERATING PARAMETERS FOR NOZZLES |
|---|---|---|---|---|---|
| ON | OFF | OFF | PROFILE 1 | X1, Y1, Z1, A1 | A1, H1, I1 |
| OFF | ON | OFF | PROFILE 2 | X2, Y2, Z2, A2 | A2, H2, I2 |
| OFF | ON | ON | PROFILE 3 | X3, Y3, Z3, A3 | A3, H3, I3 |
| OFF | OFF | OFF | PROFILE 4 | X4, Y4, Z4, A4 | A4, H4, I4 |

SYSTEM AND METHOD FOR PROTECTING A WORKSPACE FROM AIRBORNE CONTAMINANTS

BACKGROUND OF THE INVENTION

Although medical and healthcare professionals place a high priority on the health and safety of both patients and staff, the close proximity of the patient to the healthcare professionals performing services creates an environment conducive to the spread of infection. The presence of a variety of infectious airborne contaminants transmitted by the patients has become even more concerning with the pandemic conditions of the Coronavirus Disease 2019 (COVID-19). Public health officials recommend (and in some places mandate) that the mouth and nose should be covered with a cloth (or other material) face cover. As such, a common preventive measure includes the wearing of personal protective equipment (PPE) such as masks, face shields, gloves and the like, to protect from such infectious airborne contaminants. However, since PPE were originally designed with the intention of blocking blood-borne, liquid-or-solid particles, and not airborne contaminants, they do little to mitigate these risks. This is further evident by the formal references and standards for infection control, such as in the "Universal Precautions" for the medical industry, whereby nearly all such precautions related to use of PPE are geared to address blood-borne infection risks without any mention of infections caused from the airborne contaminants.

A few PPE options, such as HazMat (hazardous materials) suits, are available that safeguard its users from all contaminants including the airborne contaminants. However, such PPE options are extremely prohibitive in terms of their actual operating use, thereby rendering them irrelevant for day-to-day use, or their utility under delicate and complicated operations where maximal Degree-of-Freedom (DoF) for movement is of paramount importance.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

In one aspect, a system for protecting a workspace from airborne contaminants comprises at least one sensing capturing unit positioned within the workspace and adapted to capture a sensing data associated with the workspace, an air transmission unit adapted to direct a unidirectional flow of air, an air capturing unit adapted to receive the unidirectional flow of air directed from the air transmission unit, and a processor operatively coupled to the at least one sensing capturing unit, the air transmission unit, and the air capturing unit. The processor is configured to receive the sensing data associated with the workspace from the at least one sensing capturing unit and determine presence of at least one source of transmission of the airborne contaminants in the workspace based on the received sensing data. The processor is further configured to configure a capture zone within the workspace based on the determined at least one source of transmission of the airborne contaminants. The capture zone being an area suspected to be infected with the airborne contaminants transmitted from the determined at least one source of transmission of the airborne contaminants in the workspace. The processor is configured to control the air transmission unit to direct the unidirectional flow of air over the configured capture zone, thereby directing movement of the airborne contaminants in the capture zone and further to control the air capturing unit to capture the unidirectional flow of air, along with the airborne contaminants, directed from the air transmission unit.

In another aspect, a method for protecting a workspace from airborne contaminants comprises receiving, by a processor, a sensing data associated with the workspace captured by at least one sensing capturing unit positioned in the workspace and further determining, by the processor, presence of at least one source of transmission of the airborne contaminants in the workspace based on the received sensing data. The method further comprises configuring, by the processor, a capture zone within the workspace based on the determined at least one source of transmission of the airborne contaminants. The capture zone being an area suspected to be infected with the airborne contaminants transmitted from the determined at least one source of transmission of the airborne contaminants in the workspace. Additionally, the method comprises controlling, by the processor, an air transmission unit to direct a unidirectional flow of air over the configured capture zone, thereby directing movement of the airborne contaminants in the capture zone. The method also comprises controlling, by the processor, an air capturing unit to capture the unidirectional flow of air, along with the airborne contaminants, directed from the air transmission unit.

Figure 1:
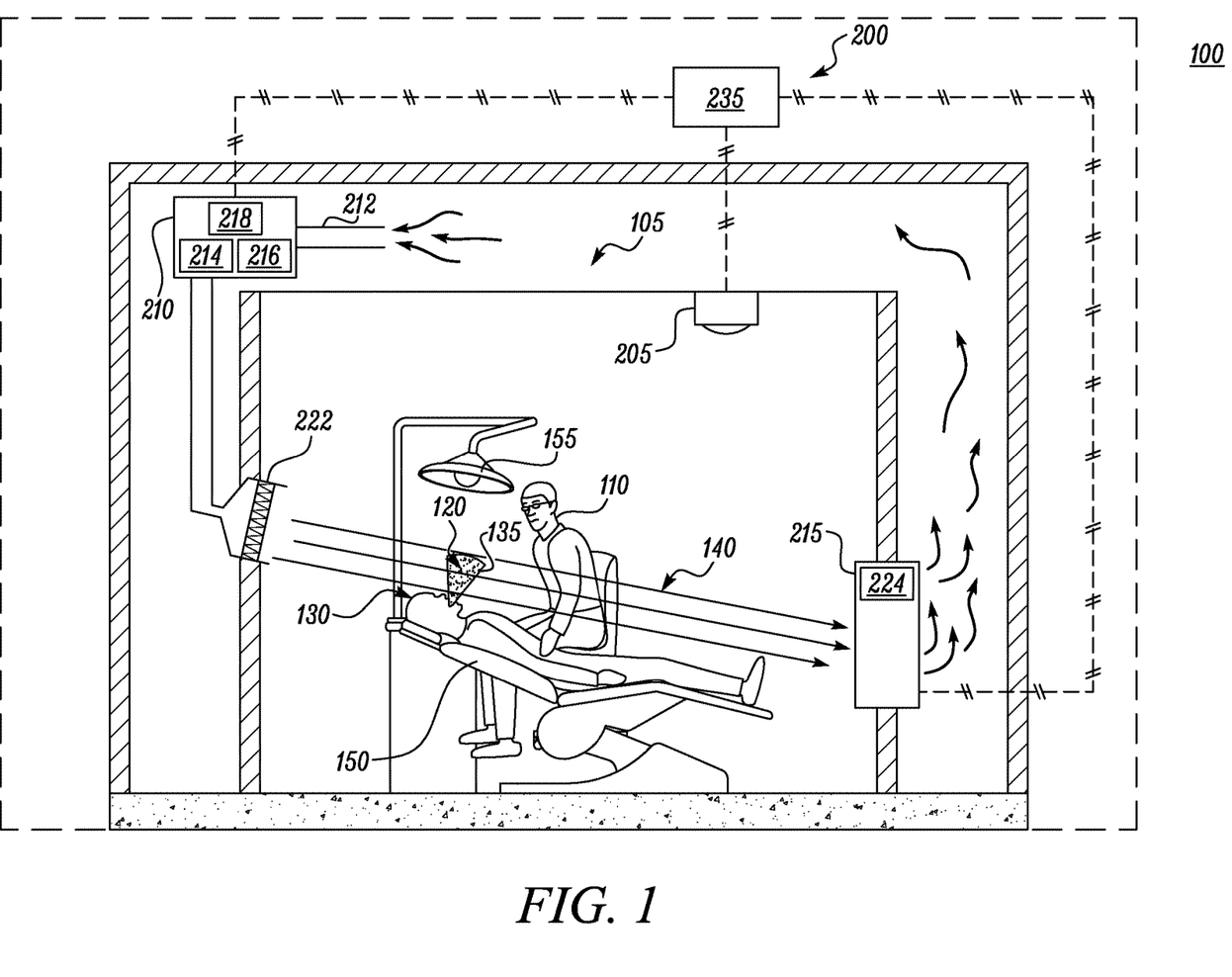
FIG. 1 illustrates a workspace environment employing an exemplary system for protecting a workspace from airborne contaminants, in accordance with some embodiments.
Figure 2:
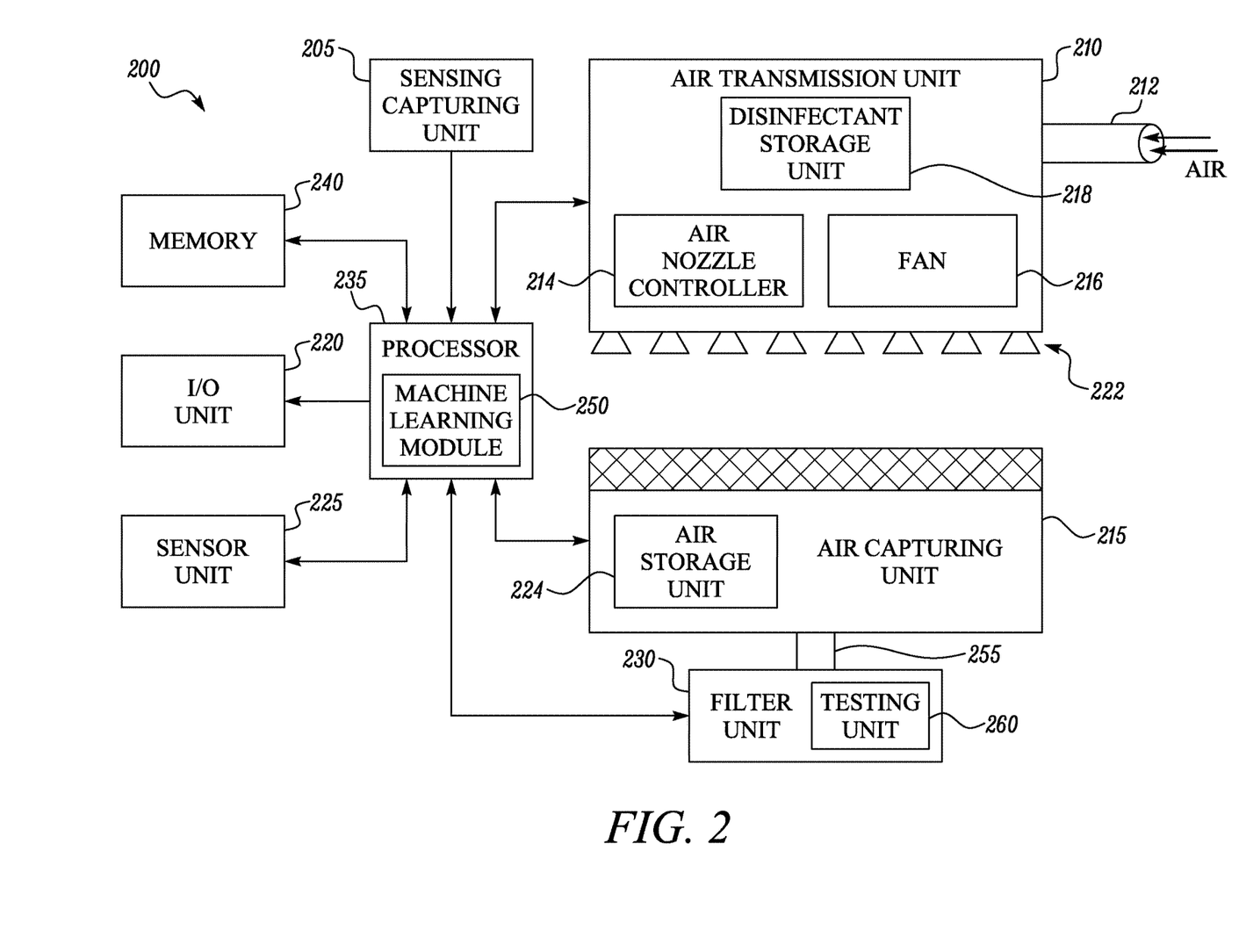
FIG. 2 illustrates a schematic block diagram of the exemplary system for protecting the workspace from the airborne contaminants, in accordance with some embodiments.

FIG. 1 illustrates a workspace environment 100 employing an exemplary system 200 for protecting a workspace 105 from airborne contaminants 120, in accordance with various embodiments. FIG. 2 illustrates a schematic block diagram of the exemplary system 200, in accordance with the various embodiments. The workspace environment 100 may be any physical environment that may require protection from airborne contaminants, such as a healthcare facility, a food packaging and processing facility, public transportation, (for example a train, bus, or subway), a shopping mall, a beauty or therapeutic services facility, or the like. The workspace 105 may be a closed space within the workspace environment 100, such as a dental or medical care facility, or any other type of closed physical space including, but not limited to, a packaging unit and/or a processing unit within the food packaging and processing facility, a retail store within the shopping mall, an office space, and a passenger compartment of the public transportation, and the like. In some embodiments, the workspace environment 100 as well as the workspace 105 may be implemented combinedly as a single space where the system 200 may be implemented. In other embodiments, the workspace environment 100 may encompass a plurality of workspaces 105. Further, the airborne contaminants 120 may be any form of contaminants including, but not limited to, droplets, fumes, mists, vapors, dust, virus particles, disease molecules, bacterium, or other types of pathogens, that may be transmitted from a source 130 of the airborne contaminants 120 within the workspace 105. In an example, as shown in FIG. 1, the source 130 of transmission of the airborne contaminants 120 is a patient seated within the workspace 105. However, it may be contemplated that the source 130 may be any living or non-living entity including, but not limited to another person, such as a practitioner 110, (for example, a dentist as illustrated), an animal, such as a pet (not shown), or a machine, such as an air circulator (not shown) present within the workspace 105.

Referring to both FIG. 1 and FIG. 2, the workspace environment 100 includes the system 200 for protecting the workspace 105 from the airborne contaminants 120 transmitted from the source 130 in the workspace 105. The system 200 may be an independent system that may be added to existing operating setups in the workspace 105 to protect the workspace 105 from the airborne contaminants 120. Alternatively, the system 200 may be integrated with the specific operations' environment of the workspace 105, for example, within a procedure table or chair 150 (for example, a dental chair as illustrated).

As depicted in FIGS. 1 and 2, the system 200 may include a sensing capturing unit 205, an air transmission unit 210, an air capturing unit 215, and a processor 235 operatively coupled to one another via one or more buses or other wired or wireless connections, as is known in the art. As shown in FIG. 2, the system 200 may also include an input/output unit 220, a sensor unit 225, a memory 240, and a filter unit 230 operatively coupled to the processor 235 via one or more buses or other wired or wireless connections, as is known in the art. Although the memory 240 and the processor 235 are shown as separate units in FIG. 2, it will be appreciated that the memory 240 and the processor 235 can be implemented together as a standalone computing system in some embodiments. Additionally, in some embodiments, the memory 240 may be formed as a part of other devices, such as the practitioner's cellular telephone or any other computing device, present in the workspace 105. Although not shown, in some embodiments, the system 200 may include a plurality of each of the sensing capturing units 205, the air transmission units 210, the air capturing units 215, and the filter units 230 depending upon the layout, the size, and other features of the workspace 105.

The sensing capturing unit 205 in some embodiments is an image sensing unit, an electromagnetic detection unit, a thermal capturing unit, a chemical capturing unit, or any other sensing capturing unit now known or later developed. The sensing capturing unit 205 is adapted to capture a sensing data associated with the workspace 105 and transmit the captured sensing data associated with the workspace 105 to the processor 235. As shown, the sensing capturing unit 205 may be operatively coupled to the processor 235. The sensing capturing unit 205 may be positioned within the workspace 105 to capture the sensing data associated with the workspace 105. For instance, in the exemplary implementation shown in FIG. 1, the sensing capturing unit 205 is vertically mounted on the ceiling within the workspace 105 to capture the sensing data of the workspace 105. The sensing capturing unit 205 may be a camera or any other device capable of capturing the sensing data of the workspace 105. The sensing data may include a sequence of images of the workspace 105 captured by the sensing capturing unit 205 over a period of time and/or any data associated with the sequence of the images of the workspace 105 captured by the sensing capturing unit 205 over the period of time. Examples of the images may include, but not limited to, two-dimensional images, three-dimensional images, and so on. For instance, in the exemplary implementation shown in FIG. 1, the images of the workspace 105 may include the images of a plurality of components, such as, the source 130, the practitioner 110, the chair 150, a light 155, and others, present within the workspace 105. In some embodiments, depending upon the layout, the size, and other features of the workspace 105, the system 200 may include more than one sensing capturing units 205, spaced a distance apart from one another in the workspace 105 to capture the sensing data of an entire area of the workspace 105.

The processor 235 is configured to receive the sensing data associated with the workspace 105 from the sensing capturing unit 205 and determine presence of at least one source 130 of transmission of the airborne contaminants 120 in the workspace 105 based on the received sensing data. The processor 235 may be located within or remotely with respect to the workspace 105. For instance, the processor 235 has been shown and described to be positioned remotely with respect to the workspace 105 in the exemplary implementation, as shown in FIG. 1, however it will be appreciated that the processor 235 may be positioned within the workspace 105, in alternative embodiments.

In accordance with various embodiments, the processor 235 may be configured to determine the presence of the source 130 of transmission of the airborne contaminants 120 based on the sensing data by employing various machine vision techniques. In an exemplary embodiment, the processor 235 is configured to analyze the received sensing data to determine physical characteristics of the plurality of components such as, the source 130, the practitioner 110, the chair 150, and the light 155 in the sensing data. The processor 235 may further be configured to identify one or more components, from the plurality of components, located within predefined areas in the sensing data. The predefined areas may be defined as areas where the source 130 of transmission of the airborne contaminants 120 is likely to be present. In the illustrated embodiment, the predefined area may include the area above the chair 150 and the one or more components located within the predefined areas may include the patient. The processor 235 may be further configured to compare the physical characteristics of the identified one or more components within the predefined areas with predetermined physical characteristics associated with known sources of transmission of airborne contaminants. The processor 235 may then be configured to identify a component, from the one or more components, as the source 130 of the transmission of the airborne contaminants 120 when the physical characteristics of the component match the predetermined physical characteristics associated with the known sources of transmission of airborne contaminants. In the exemplary implementation, the processor 235 may compare the physical characteristics of the patient with the predetermined physical characteristics associated with known sources (such as, a human) and identifies the patient as the source 130 of transmission of the airborne contaminants 120 when the physical characteristics of the patient match the predetermined physical characteristics of the human. In some embodiments, the processor 235 may be further configured to identify the mouth and nose of the patient as a point of transmission of the airborne contaminants 120 from the source 130, using various machine vision techniques, such as object detection and face recognition techniques, now known or future developed.

The processor 235 may additionally use Artificial Intelligence (AI) based techniques, now known or future developed, to identify the source 130 within the sensing data. For example, in some embodiments, the processor 235 will set an initial configuration associated with the workspace 105. Thereafter, the processor 235 may use artificial intelligence techniques in a continuous loop for real-time feedback and training of source identification. The processor 235 continually evolves the specifics in real time with new inputs to continually optimize techniques to identify the source 130 over time.

Although the machine vision technique is described herein to determine the presence of the source(s) of transmission of the airborne contaminants, other techniques for determining the presence of the source(s) of transmission of the airborne contaminants in the workspace 105 may also be used in alternative implementations.

In one embodiment, the processor 235 is adapted to configure a capture zone 135 within the workspace 105 based on the determined source 130 of transmission of the airborne contaminants 120. The capture zone 135 may be an area suspected to be infected with the airborne contaminants 120 transmitted from the determined source 130 in the workspace 105. The capture zone 135 may also be defined as an area/zone that is to be secured and rendered harmless in order to protect the workspace 105 from the airborne contaminants 120. For example, the capture zone 135 may be defined as an area within a predetermined radial distance from and around the source 130, in this case, front and sides of the mouth and nose of the determined source 130 of the airborne contaminants 120. In some embodiments, the predetermined radial distance corresponds to a minimum separation distance required from the source 130 of transmission of the airborne contaminants 120, such as the patient, to protect others from getting infected by the airborne contaminants 120 transmitted from the source 130. The predetermined radial distance may be predefined according to the specific requirements of the workspace 105. For example, the predetermined radial distance may be set corresponding to the layout, the size and other features of the workspace 105. In one non limiting example, the predetermined radial distance may be predefined as one (1) meter from the front and sides of the mouth and nose of the determined source 130 of the airborne contaminants 120. Accordingly, the capture zone 135 may be defined so as to cover this predetermined area around the source 130. As depicted in FIG. 1, the capture zone 135 may be conical in shape. Alternatively, the capture zone 135 may be configured to be of any other shape, including rectangular, circular, and the like.

In some embodiments, the processor 235 may be configured to define exclusion and/or inclusion areas based on a location of the determined source 130 of the airborne contaminants 120 in the workspace 105. The inclusion areas may include areas suspected to be including the airborne contaminants 120, while the exclusion areas may include areas free from the airborne contaminants 120. For example, the inclusion area may include, but not limited to, an area adjacent to the mouth and nose of the source 130 of the airborne contaminants 120 and the exclusion area may include, but not limited to, an area away from the source 130 of the airborne contaminants 120. In some embodiments, the processor 235 may be adapted to configure the capture zone 135 based on the defined exclusion and/or inclusion areas. In some embodiments, the processor 235 may be adapted to configure the capture zone 135 to include all inclusion areas. In some alternative embodiments, the processor 235 configures the capture zone to include all inclusion areas and few exclusion areas.

In accordance with various embodiments, the processor 235 may be further adapted to adjust the configured capture zone 135 based on an operating state of one or more devices operable within the workspace 105. The operating state of each of the one or more devices may define the active or inactive state of the device. To this end, the processor 235 may be adapted to detect the one or more devices within the workspace 105, along with the operating state of each of the detected one or more devices. In some embodiments, when the system 200 is integrated with the specific operations' environment of the workspace 105, the one or more devices may each be individually communicatively coupled to the processor 235 and the processor 235 may be configured to determine an operating state of each of the one or more devices based on signals received from the one or more devices. The signals received from the one or more devices may include the identification information of the corresponding device along with other information indicative of the operating state of the associated device. In yet other embodiments, when the system 200 is added as add-on to the existing operating setups, the processor 235 may be configured to determine the identification information and the operating state of the one or more devices based on various machine vision techniques applied on the sensing data generated by the sensing capturing unit 205.

Figure 3:
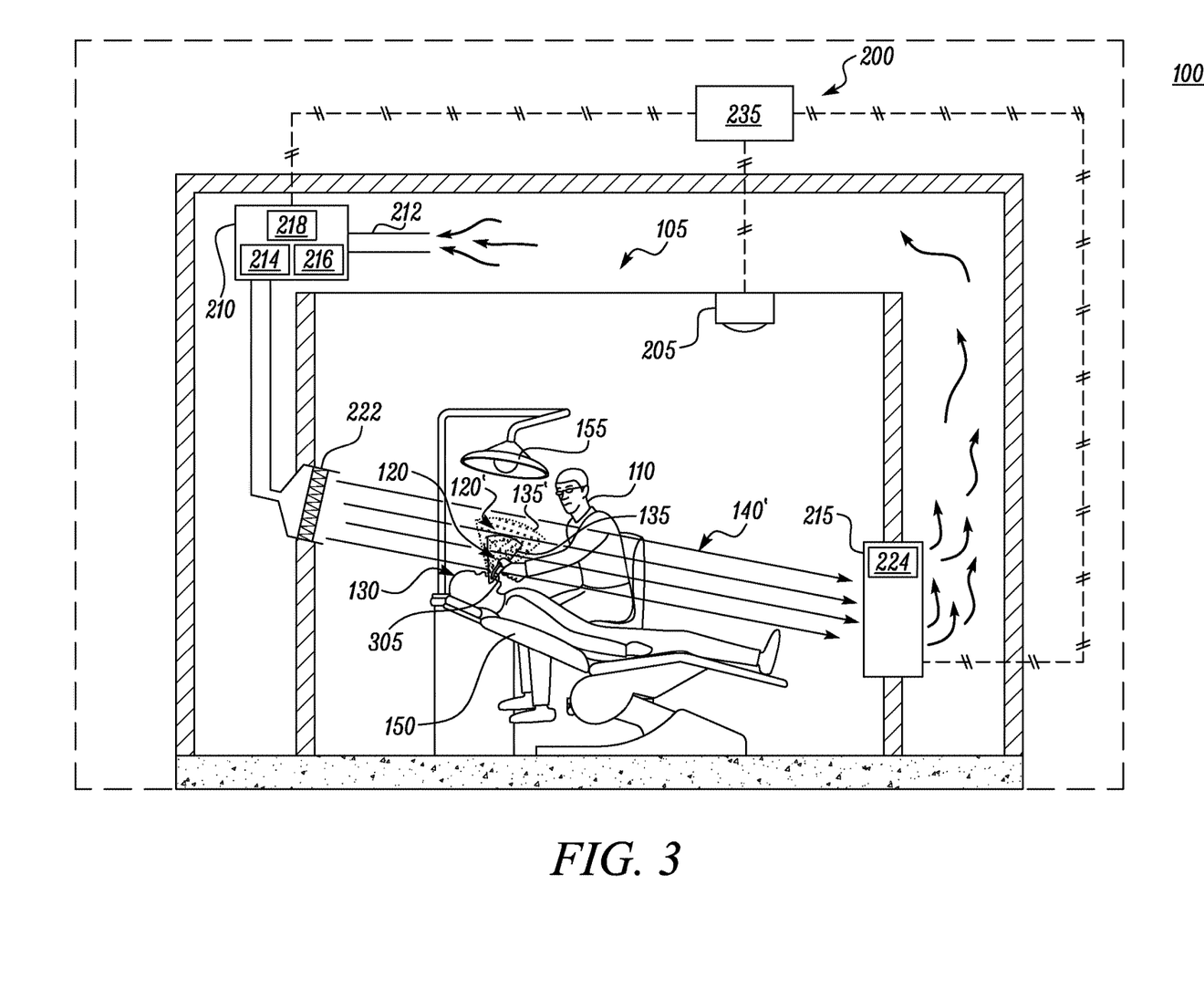
FIGS. 3 and 4 illustrate the exemplary system employed within the workspace environment, in accordance with some additional embodiments.
Figure 5:
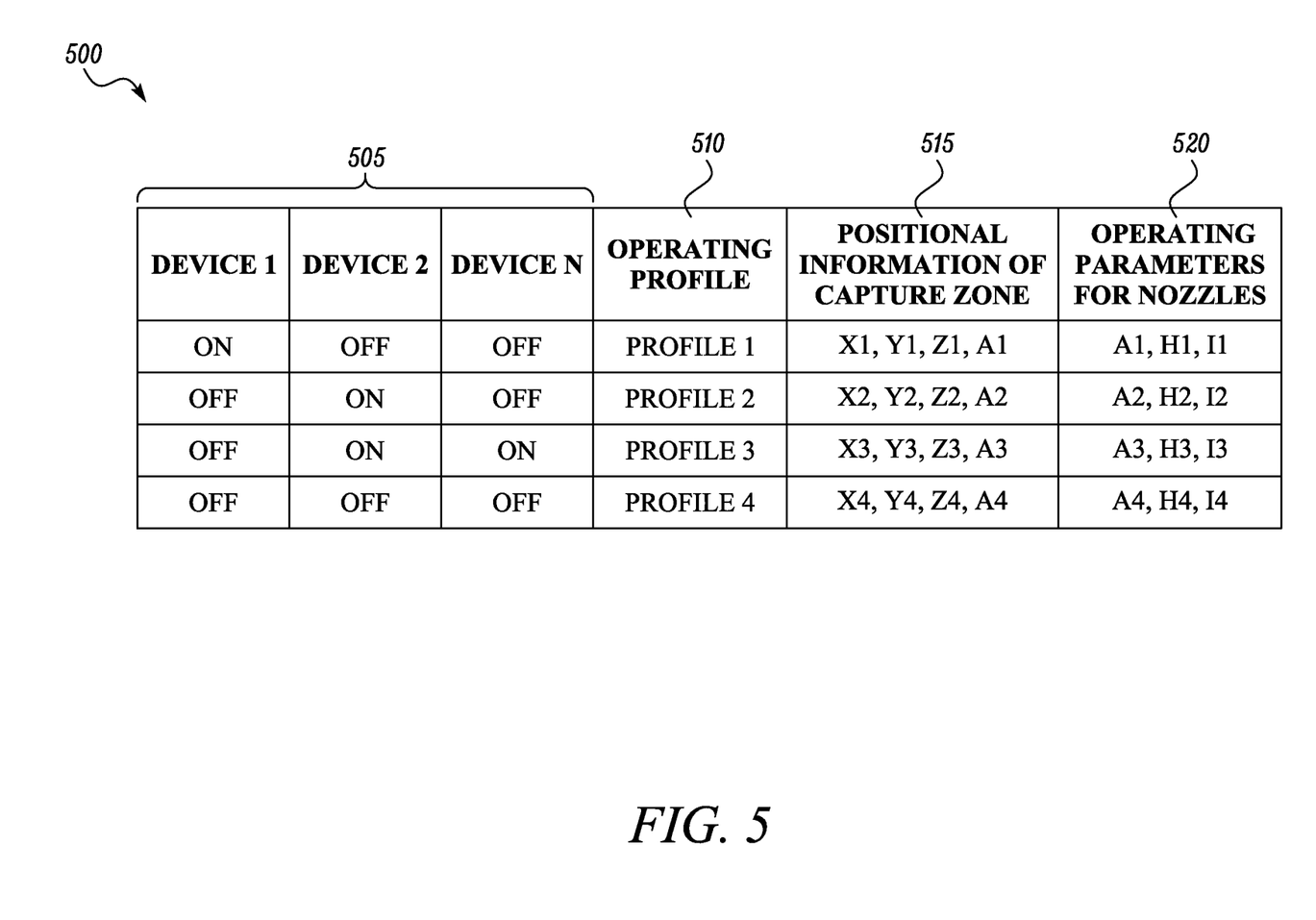
FIG. 5 illustrates data stored in the exemplary system for protecting the workspace from the airborne contaminants, in accordance with some embodiments.

In some scenarios, the airborne contaminants (shown by reference numeral 120' in FIG. 3) may spread to a larger area due to a change in the operating state of a device present within the workspace 105. For example, when a device, such as an air gun 305 is activated and being operated on the source 130 of the airborne contaminants, such as the patient, the intensity of flow of air escaping from the mouth and nose of the source 130 increases thereby causing the airborne contaminants 120' to spread to the larger area as compared to the previously configured area of the capture zone 135, as illustrated in FIG. 3. To this end, the processor 235 may be configured to adjust the capture zone 135 to a capture zone 135' (as shown in FIG. 3) to include the larger area with the airborne contaminants 120'. In some embodiments, the processor 235 may be configured to determine the configuration of the capture zone 135' based on predefined and pre-stored configurations corresponding to the identification information of the activated one or more devices in the memory 240. The memory 240, as shown in FIG. 5, may be configured to store various configurations for capture zones corresponding to various operating states of the one or more devices operable within the workspace 105. For instance, the memory 240 may store positional information 515 of the capture zone 135' corresponding to an operating state 505 of each of the one or more devices within the workspace 105. The positional information 515 of the capture zone 135' may include the position coordinates (X, Y, Z coordinates) and the size (for example, an area A1) of the capture zone 135'. The processor 235 may be further configured to adjust the capture zone 135 to the capture zone 135' according to the predefined configurations of capture zone 135' stored in the memory 240 to capture the airborne contaminants 120' when the air gun 305 is detected to be in active state by the processor 235.

Furthermore, the capture zone 135' may be different for different devices within the workspace 105 and may be determined based on operating characteristics of the activated one or more devices in the workspace 105. For instance, the capture zone 135' associated with the usage of the air gun 305 may be larger than a capture zone associated with the usage of dental syringe, as the flow of air escaping from the mouth and nose of the patient due to the usage of the air gun 305 may be greater as compared to the flow of air escaping from the mouth and nose of the patient when the dental syringe is used.

In some embodiments, the positional information 515 of the capture zone 135, 135' may be stored as separate operating profiles in the memory 240. To this end, the memory 240 of the system 200 may be configured to store data 500 (as shown in FIG. 5) associated with each of the one or more devices operational within the workspace 105. For example, the data 500 may include the operating state 505 of each of the one or more devices and an operating profile 510 of the workspace 105 based on the operating state 505 of each of the one or more devices. For example, when the operating state of all devices in the workspace 105 represent inactive state, the operating profile 510 of the workspace 105 may be referred to as a resting profile. Similarly, when the operating state of the one or more devices, such as the air gun 305 (shown in FIG. 3) in the workspace 105 represents active state, the operating profile 510 of the workspace 105 may be referred to as the air gun profile. The memory 240 may be further configured to store the positional information 515 of the capture zone 135' for each operating profile 510 of the workspace 105. In some embodiments, the positional information 515 corresponding to the operating state 505 of each of the one or more devices within the workspace 105 and/or the operating profile 510 are calibrated and validated before being stored in the memory 240. In such embodiments, the processor 235 may be first configured to determine the operating profile 510 of the workspace 105 and the positional information 515 of the capture zone 135' based on the determined operating state 505 of the one or more devices. The processor 235 may further be configured to adjust the capture zone 135 to the capture zone 135' based on the determined positional information 515. In an embodiment, the components of the system 200 may be calibrated and validated during the initial set-up in the workspace 105 so as to accurately configure the capture zone 135 corresponding to the layout, the size and other features of the workspace 105.

Figure 4:
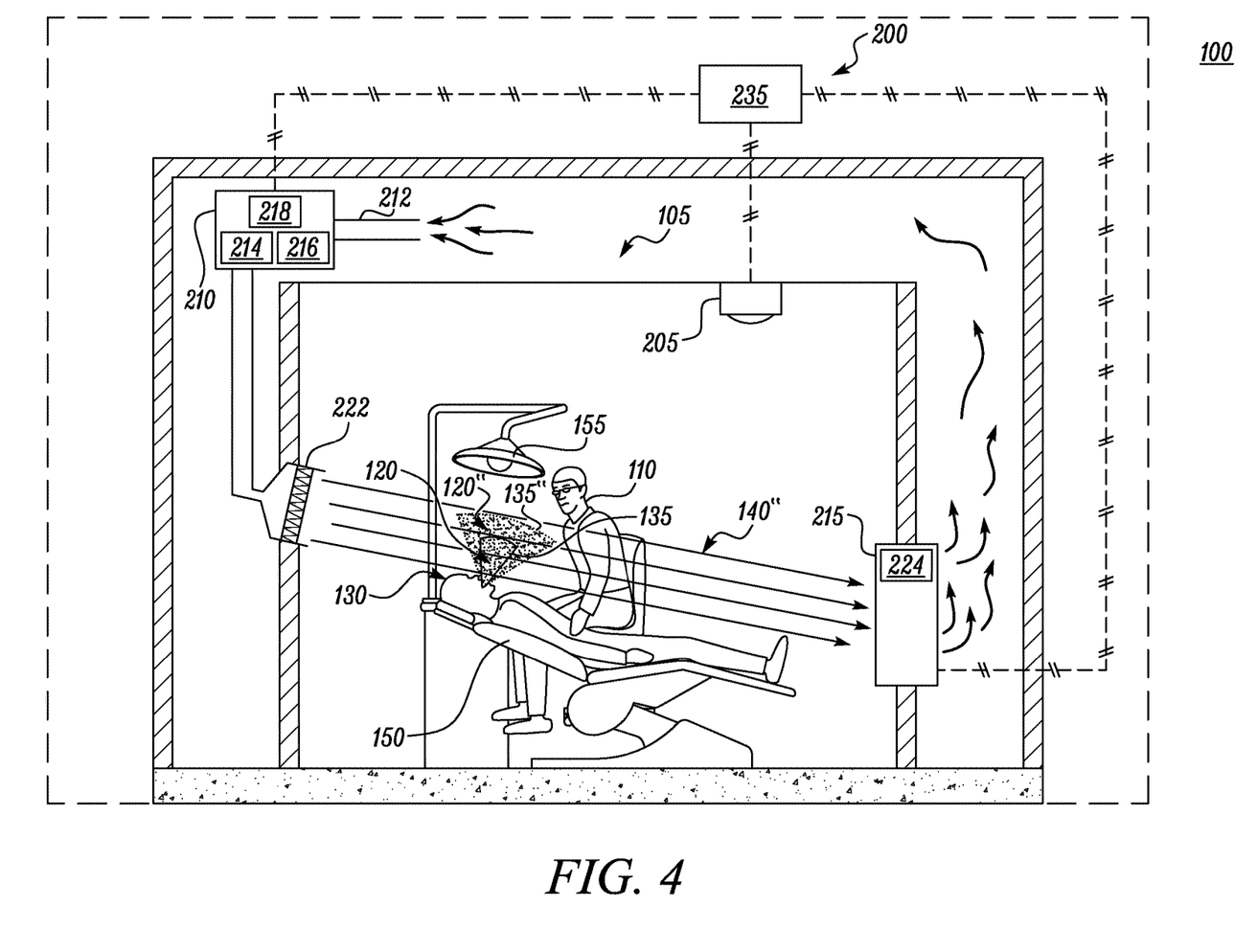

In accordance with various embodiments, the processor 235 may be configured to alternatively or additionally adjust the capture zone 135, 135' based on a distribution pattern of the airborne contaminants within the workspace 105, as illustrated in FIG. 4. In some scenarios, the airborne contaminants (as shown by reference numeral 120" in FIG. 4) may also be present outside the capture zone 135, 135', such as due to malfunctioning of the air transmission unit 210, the air capturing unit 215, and the filter unit 230 of the system 200, or activation of additional equipment (such as, an air conditioner or an air fan) that cause the airborne contaminants 120, 120' to spread outside the capture zone 135, 135', or some unexpected circumstances, or any other known or unknown reasons. To protect the workspace 105 from the airborne contaminants 120" that do not lie within the capture zone 135, 135', the processor 235 may be configured to determine the distribution pattern of the airborne contaminants 120" in the workspace 105 and adjust the capture zone 135, 135' to a capture zone 135" to include an area with the airborne contaminants 120" based on the determined pattern.

To this end, the sensor unit 225 is operatively coupled to the processor 235. The sensor unit 225 may be configured to detect the presence of the airborne contaminants 120" in the workspace 105. The sensor unit 225 may be positioned anywhere within the workspace 105. For example, the sensor unit 225 may be positioned closer to areas suspected to be infected with the airborne contaminants, such as near the chair 150. Alternatively, the sensor unit 225 may be positioned overhead the chair 150, such as near the light 155. Examples of the sensor unit 225 may include, but not limited to, one or more of a thermal sensor, internet of things (IoT) sensors, a vapor sensor, a chemical sensor, a visual sensor, and a biological sensor.

The processor 235 may be configured to determine the distribution pattern of the airborne contaminants 120" in the workspace 105 based on the detected presence of the airborne contaminants 120" and further determine whether the detected airborne contaminants 120" are captured within the configured capture zone 135, 135'. If the detected airborne contaminants 120" are determined to be captured within the configured capture zone 135, 135', the processor 235 may not adjust the capture zone 135, 135' any further. However, if the detected airborne contaminants 120" are determined to be present outside and not captured within the configured capture zone 135, 135', the processor 235 may be configured to further adjust the previously configured capture zone 135, 135' to the capture zone 135" (as shown in FIG. 4) so as to include the airborne contaminants 120". In accordance with various embodiments, the processor 235 may be configured to continuously detect the distribution pattern of the airborne contaminants 120" in the workspace 105 and adjust the capture zone 135, 135' to capture the airborne contaminants 120" within the adjusted capture zone 135", in real time. In some embodiments, a positional information of the adjusted capture zone 135" may be stored in the memory 240, for future reference and use.

In an embodiment, the processor 235 is further configured to control the air transmission unit 210 to direct a unidirectional flow of air 140, 140', 140" over the configured capture zone 135, 135', 135" (as shown in FIGS. 1, 3, and 4). In accordance with various embodiments, the air transmission unit 210 may be adapted to direct the unidirectional flow of air 140, 140', 140" over the capture zone 135, 135', 135" and direct movement of the airborne contaminants 120, 120', 120" in the capture zone 135, 135', 135" towards the air capturing unit 215 positioned opposite to the air transmission unit 210 within the workspace 105.

Referring back to FIGS. 1 and 2, in an exemplary embodiment, the air transmission unit 210 may be operatively coupled to the processor 235. The air transmission unit 210 includes a conduit 212, an air nozzle controller 214, a fan 216, a disinfectant storage container 218, and one or more nozzles 222. In some implementations, the fan 216 and the one or more nozzles 222 may be positioned anywhere within the workspace 105, depending upon the requirement of the workspace environment 100. In the exemplary implementation, as illustrated, the fan 216 and the one or more nozzles 222 may be positioned above the head of the patient sitting on chair 150. The conduit 212 may be concealed and positioned outside the workspace 105, such as in the walls and false ceiling of the workspace environment 100, as shown in FIG. 1.

The fan 216 and the one or more nozzles 222 are fluidly coupled to the conduit 212, and the processor 235 may be configured to control the fan 216 to draw air in from an environment outside the workspace 105 through the conduit 212 and generate a flow of air through the one or more nozzles 222. In an exemplary embodiment, the processor 235 may be configured to direct the flow of air generated by the fan 216 unidirectionally through the one or more nozzles 222 over the capture zone 135, 135', 135" so as to entirely cover the capture zone 135, 135', 135", as shown in FIGS. 1, 3, and 4. In accordance with various embodiments, the unidirectional flow of air 140, 140', 140" directed over the capture zone 135, 135', 135" directs the movement of the airborne contaminants 120, 120'. 120" present in the configured capture zone 135, 135', 135" towards the air capturing unit 215, thereby forming an air curtain over the capture zone 135, 135', 135". In the embodiment, as shown in FIGS. 1, 3, and 4, the unidirectional flow of air 140, 140'. 140" is indicated as diagonal flow of air. However, it may be contemplated that depending on the positioning of the air transmission unit 210 and the air capturing unit 215, the unidirectional flow of air 140, 140', 140" may include vertical or horizontal flow of air, without deviating from the scope of the claimed subject matter. In some embodiments, when the additional equipment (such as, the air conditioner or the air fan) that may impact the movement of the airborne contaminants 120, 120', 120" are present within the workspace 105, the processor 235 may be configured to adjust the capture zone 135, 135', 135" to capture an area with the airborne contaminants 120, 120', 120" and then direct the unidirectional flow of air 140, 140', 140" over the adjusted capture zone to direct the airborne contaminants 120, 120', 120" towards the air capturing unit 215.

In some embodiments, the processor 235 may also be configured to determine one or more operating parameters of the one or more nozzles 222 and adjust the same according to the configured capture zone 135, 135', 135". To this end, as shown in FIG. 5, the memory 240 may also be configured to store operating parameters 520 of the one or more nozzles 222 corresponding to each operating profile 510 of the workspace 105. The operating parameters of the one or more nozzles 222 may include, but not limited to, data related to an angle (for example, A1), a height (for example, H1), and an intensity (for example, I1) at which the one or more nozzles 222 should operate to direct the unidirectional flow of air 140, 140', 140" over the capture zone 135, 135', 135". For example, the operating parameters 520 of the one or more nozzles 222 may be defined based on the positional information of the capture zone 135, 135', 135" so as effectively generate the flow of air 140, 140'. 140" that successfully directs the airborne contaminants 120, 120', 120" in the capture zone 135, 135', 135" towards the air capturing unit 215. In some alternative embodiments, the processor 235 may also selectively activate and deactivate one or more nozzles within the one or more nozzles 222 to adjust the flow of air according to the configured capture zone. In some embodiments, operating parameters of the one or more nozzles 222 corresponding to the operating state 505 of each of the one or more devices within the workspace 105 and/or the operating profile 510 are calibrated and validated before being stored in the memory 240.

The processor 235 may be configured to determine the operating parameters 520 of the one or more nozzles 222 corresponding to the operating profile 510 of the workspace 105 based on the data 500 stored in the memory 240 and control the air nozzle controller 214 to adjust the one or more nozzles 222 based on the determined operating parameters 520. The air nozzle controller 214 may be configured to, in turn, individually control each of the one or more nozzles 222, for example, the angle, the height, and the intensity of each of the one or more nozzles 222. The air nozzle controller 214 may be located within or outside the workspace 105. Once all the nozzles 222 are adjusted according to the determined operating parameters 520, the processor 235 may be configured to control the air nozzle controller 214 to direct the flow of air 140, 140', 140" generated by the fan 216 unidirectionally over the capture zone 135, 135'. 135" through the one or more nozzles 222.

Further, in some embodiments, the processor 235 may also be configured to adjust the operating parameters 520 of the one or more nozzles 222 based on the determined distribution pattern of the airborne contaminants 120, 120', 120" present in the workspace 105. For instance, the processor 235 may be configured to determine that the at least one of the operating parameters 520 of the one or more nozzles 222 be adjusted by a first predefined amount when the distribution pattern of the airborne contaminants 120, 120', 120" represent that a density of the airborne contaminants 120, 120', 120" in the capture zone 135, 135', 135" is greater than or equal to a threshold value. In such a scenario, for example, the intensity (such as, the speed, the range, and the pressure etc.) of flow of air 140, 140', 140" directed from the one or more nozzles 222 may be increased to effectively remove the airborne contaminants 120, 120' 120" from the capture zone 135, 135', 135". In another example when the determined distribution pattern of the airborne contaminants 120, 120', 120" indicates a narrow spread of contaminants but the density of contaminants is high, then the processor 235 may adjust the angle and intensity of the one or more nozzles 222, and/or selectively activate only a few of the one or more nozzles 222 to direct a narrow and high intensity flow of air over the capture zone.

In some embodiments, the processor 235 may be configured to control the disinfectant storage container 218 in the air transmission unit 210 to disperse disinfectant over the capture zone 135, 135', 135". The disinfectant storage container 218 may be configured to store and inject disinfectants, such as chemicals, for disinfecting the airborne contaminants 120, 120', 120" present in the workspace 105. The disinfectant storage container 218 may be positioned within or outside the workspace 105. In accordance with various embodiments, the processor 235 may be configured to control the disinfectant storage container 218 in the air transmission unit 210 to disperse disinfectant, along with the unidirectional flow of air 140, 140', 140", through the one or more nozzles 222 over the capture zone 135, 135', 135". The disinfectant dispensed along with the unidirectional flow of air 140, 140', 140" transmits over the capture zone 135, 135', 135" and disinfects the airborne contaminants 120, 120', 120" present in the capture zone 135, 135', 135".

The processor 235 may be further configured to control the air capturing unit 215 to capture the unidirectional flow of air 140, 140', 140" along with the airborne contaminants 120, 120', 120" directed from the air transmission unit 210. The air capturing unit 215 may be adapted to receive the unidirectional flow of air 140, 140', 140" directed from the one or more nozzles 222 of the air transmission unit 210. In accordance with various embodiments, the air capturing unit 215 may be operatively coupled to the processor 235. The air capturing unit 215 may be positioned opposite and in line with the air transmission unit 210 to receive the unidirectional flow of air 140, 140', 140" directed from the one or more nozzles 222 of the air transmission unit 210. The air capturing unit 215 may be positioned anywhere within the workspace 105, for example, on a side wall shown in FIG. 1. However, in some alternative embodiments, the air capturing unit 215 may also be positioned closer to the source 130, such as closer to the chest of the patient, so as to reduce the length of the air curtain and thus, immediately capture the airborne contaminants 120, 120', 120" transmitted from the source 130. Further, the size of the air capturing unit 215 may be varied depending upon the requirements of the workspace 105. In some embodiments, the air capturing unit 215 may be sized to cover a single chair 150 (as shown in FIG. 1), while in alternative embodiments, the air capturing unit 215 may be sized to cover multiple chairs in the workspace 105. In some other embodiments, the air capturing unit 215 may be positioned via a moveable mounting system that may facilitate adjustment of the air capturing unit 215 as and when required.

In an embodiment, the air transmission unit 210 and the air capturing unit 215 of the system 200 may be calibrated and validated during the initial set-up in the workspace 105 so as to accurately generate the flow of air 140, 140', 140' over the capture zone 135, 135', 135" corresponding to the layout, the size and other features of the workspace 105. In an exemplary embodiment, the air capturing unit 215 may be a vacuum or a suction unit configured to draw the unidirectional flow of air 140, 140', 140" directed from the one or more nozzles 222 along with the airborne contaminants 120, 120', 120" from the capture zone 135, 135', 135". In some embodiments, the processor 235 may be configured to control the air nozzle controller 214 to electrically charge or polarize air ions in the unidirectional flow of air 140, 140', 140" directed towards the capture zone 135, 135', 135". In some embodiments, the electrically charged or polarized air ions are generated by placing electrically charged materials adjacent to the one or more nozzles 222. The electrically charged or polarized air ions attach to the airborne contaminants 120, 120', 120" present in the capture zone 135, 135', 135" and force the airborne contaminants 120, 120', 120" to enter the air capturing unit 215. In some embodiments, the air capturing unit 215 may also include electrically and opposite charged materials to capture the electrically charged or polarized air ions attached to the airborne contaminants 120, 120', 120".

In some embodiments, the air capturing unit 215 may also include an air storage container 224 to store air samples collected from the captured flow of air 140, 140', 140" along with the airborne contaminants 120, 120', 120". In accordance with various embodiments, the processor 235 may be configured to control the air capturing unit 215 to store air samples from the captured flow of air 140 along with the airborne contaminants 120, 120', 120" in the air storage container 224. In some embodiments, the stored air samples may be stored with other relevant parametric data, such as, time, date, and identification information of the individuals present in the workspace 105 and the collected sample. These stored air samples may be maintained for each patient for various purposes, such as archival, test, investigation, tracing, further analysis, or record. For example, these samples may be used subsequently to test and determine the type of contaminants transmitted by the source 130. The processor 235 may communicate such information to the patient, in some embodiments, to alert them of any potential disease or infection based on the determined type of contaminant. Such information may also facilitate tracing of potential transmission sources in case of epidemic or pandemic like situations.

In some embodiments, the filter unit 230 may be configured to receive the unidirectional flow of air 140, 140', 140" along with the airborne contaminants 120, 120', 120" captured by the air capturing unit 215 through a conduit 255 fluidly connected to the air capturing unit 215. The filter unit 230 may be operatively coupled to the processor 235 and located within or remotely with respect to the workspace 105. Upon receiving the unidirectional flow of air 140, 140', 140" along with the airborne contaminants 120, 120', 120", the processor 235 may be configured to control the filter unit 230 to disinfect the captured airborne contaminants 120, 120', 120". To this end, the processor 235 may be configured to determine types of the captured airborne contaminants 120, 120', 120", using the filter unit 230. In some embodiments, the determined types of the captured airborne contaminants 120, 120', 120" may include toxicity and risk level of the captured airborne contaminants. Further, the processor 235 may be configured to control the filter unit 230 to disinfect the captured airborne contaminants 120, 120', 120" based on the determined types of the captured airborne contaminants 120, 120', 120". In an exemplary embodiment, the filter unit 230 may be configured to disinfect the captured airborne contaminants 120, 120', 120" using appropriate disinfectants, such as, but not limited to, chemical disinfectants (such as alcohol, antiviral solutions), ultraviolet (UV) lights, thermal disinfection, or other filtration methods now known or future developed. In accordance with various embodiments, the filter unit 230 is designed to withstand repeated cycles of (chemical, light, and thermal) treatment to be reusable, or replaceable.

In some embodiments, the filtered air from the filter unit 230 may be recirculated back into the workspace 105. In alternative embodiments, the filtered air from the filter unit 230 may be released in the environment outside the workspace 105. In accordance with some embodiments, the captured airborne contaminants 120, 120', 120" are disinfected until the maximal tolerance limit of the airborne contaminants 120, 120', 120" is exceeded, before the treated air is recycled and released. In some embodiments, the treated air may subsequently be tested for safety, using the testing unit 260, prior to release or recirculation. In accordance with some embodiments, the testing unit 260 may be configured to test the treated air based on specific requirements for the workspace 105 and various standard regulations that may emerge in the future for the workspace 105. In yet other alternative embodiments, the filtered air from the filter unit 230 may be stored in a storage unit (not shown) for further treatment and processing.

In some embodiments, the processor 235 may be configured to configure treatment fields between the air transmission unit 210 and the air capturing unit 215, depending upon the types of the airborne contaminants 120, 120', 120". To this end, the processor 235 may be configured to determine, using the filter unit 230, a type of airborne contaminants 120, 120', 120" present in the workspace 105. The processor 235 may be further configured to determine the distribution pattern of the airborne contaminants 120, 120', 120" based on data received from the sensor unit 225. Depending upon the type and the distribution pattern of the airborne contaminants 120, 120', 120", the processor 235 may be adapted to configure treatment fields between the air transmission unit 210 and the air capturing unit 215 to disinfect the airborne contaminants 120, 120', 120". In accordance with some embodiments, the treatment fields are configured to provide one or more of the ultraviolet radiations, thermal heat, or other treatment techniques to disinfect the airborne contaminants 120, 120', 120". In some embodiments, the processor 235 may be configured to use machine learning models to continuously adjust the characteristics, such as light intensity, temperature etc., of the treatment fields in real time based upon the type and the distribution pattern of the airborne contaminants 120, 120', 120", as described in detail in the forthcoming disclosure.

In some embodiments, the processor 235 may be configured to periodically monitor the operational status of the various components of the system 200. For instance, the processor 235 may be configured to regularly monitor the operational status of each of the air transmission unit 210, the air capturing unit 215, and the filter unit 230 to detect malfunctioning of any one or more of these components. In accordance with various embodiments, the malfunctioning of a unit may be defined as a state when an operating performance of the corresponding unit falls below a defined performance threshold value or when the operating profile 510 of the workspace 105 stray from the operating profile 510 defined in the memory 240. The operating performance is the degree of effectiveness by which the respective units are functioning. For example, the processor 235 may be configured to determine the degree of effectiveness of the filter unit 230 by installing a testing unit 260 in the filter unit 230 to determine whether the captured airborne contaminants 120, 120', 120" are successfully disinfected. Similarly, the processor 235 may be configured to determine the degree of the effectiveness of the air transmission unit 210 and the air capturing unit 215 by installing various sensors in the air transmission unit 210 and the air capturing unit 215. For example, a first pressure sensor (not shown) may be installed in the air transmission unit 210 to determine whether the required intensity of flow of air is generated by the air transmission unit 210. Similarly, a second pressure sensor (not shown) may be installed in the air capturing unit 215 to determine whether the required intensity of flow of air is captured by the air capturing unit 215. The processor 235 may then be configured to determine whether the effectiveness of any of the air transmission unit 210, the air capturing unit 215, and the filter unit 230 has fallen below the defined performance threshold value. If the processor 235 determines that the effectiveness of any of the air transmission unit 210, the air capturing unit 215, and the filter unit 230 has fallen below the defined performance threshold value, the processor 235 identifies the corresponding unit that has malfunctioned and generates an alert indicative of the detected malfunctioning using the input-output unit 220 located within the workspace 105. Examples of the alerts may include, but not limited to, an audio alert, visual alert, textual alert, and so on. Such information and alerts may be subsequently used to run diagnostics on the system 200 and facilitate repair of the one or more malfunctioned components.

In some embodiments, the processor 235 may preemptively switch to safe operating profiles, such as the resting profile, in case any malfunctioning of one of the air transmission unit 210, the air capturing unit 215, and the filter unit 230 is detected. For example, the processor 235 may prevent or recommend against, via alerts, any unintended activation of aggressive operations (i.e., blow of excessive air, splash of high-pressure water, drilled particles that falls outside the capture zone 135, 135', 135" and so on) from the one or more devices within the workspace 105.

In some embodiments, the processor 235 may be configured to control the operating state of the one or more devices when the malfunctioning of any one or more of the air transmission unit 210, the air capturing unit 215, and the filter unit 230 is detected. For example, the processor 235 may be configured to change or recommend changes, via alerts, to the operating state of the devices in the workspace 105 to inactive state, to avoid any further transmission of the airborne contaminants 120" when the processor 235 detects the malfunctioning of one or more of the air transmission unit 210, the air capturing unit 215, and the filter unit 230.

In alternative embodiments, the processor 235 may also be configured to control operating characteristics of the one or more devices in order to avoid transmission of the airborne contaminants 120, 120', 120" outside the capture zone 135, 135', 135". The operating characteristics may include pressure of flow of air generated by the device, pressure of flow of water generated by the device, power state at which the device is being operated, and so on. For example, in some embodiments, after the capture zone 135, 135', 135" is configured or adjusted, a change in the operating characteristics of a device may change the flow of air escaping from the mouth and nose of the source 130 of the airborne contaminants 120, 120', 120", thereby causing the airborne contaminants 120, 120', 120" to be transmitted outside the capture zone 135, 135'. 135" in some cases. For example, an increase in the pressure of flow of air generated by the air gun 305 may also increase the flow of air escaping from the mouth and nose of the patient and cause the airborne contaminants 120, 120', 120" to be transmitted outside the capture zone 135, 135', 135". To avoid any such situation, the processor 235 may be configured to control the operating characteristics of the one or more devices, such as the air gun 305, within a predefined limit, so that any unexpected change in the operating characteristics of the one or more devices does not cause the airborne contaminants 120, 120', 120" to be transmitted outside the capture zone 135, 135', 135".

In some embodiments, the processor 235 may be configured to use machine learning models to create new operating profiles and/or adjust the existing operating profiles 510. The processor 235 may further be configured to define/adjust the positional information 515 of the capture zone 135, 135', 135" and the operating parameters 520 for the one or more nozzles 222 for each of the new and adjusted operating profiles 510. To this end, the processor 235 may additionally include a machine learning module 250 configured to be trained for detecting the machine operations by using one or more machine learning algorithms.

The machine learning module 250 may be configured to execute the instruction stored in the memory 240, to perform one or more predetermined operations. The machine learning module 250 may be a data processor and/or a mainframe employing artificial intelligence (AI) to perform the one or more predetermined operations, in accordance with some embodiments. In some embodiments, the machine learning module 250 may be implemented separately as a different unit from the processor 235 in the system 200. However, in some alternative embodiments, the machine learning module 250 may be a specially constructed computing platform for carrying out the predetermined operations as described herein. The machine learning module 250 may be implemented or provided with a wide variety of components or systems (not shown), including one or more of memories, registers, and/or other data processing devices and subsystems.

The machine learning module 250 may be any system configured to learn and adapt itself to do better in changing environments. The machine learning module 250 may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. In an exemplary embodiment, the machine learning module 250 may employ a random forest algorithm to learn and adapt itself.

The machine learning module 250 may implement an iterative learning process. The learning may be based on a wide variety of learning rules or training algorithms. The learning rules may include one or more of back-propagation, patter-by-pattern learning, supervised learning, and/or interpolation. As a result of the learning, the machine learning module 250 may learn to operate in the workspace 105.

The machine learning module 250 may be configured to receive a training data set comprising the data 500 associated with the operating state 505 of each of the one or more devices, the operating profile 510 of the workspace 105, the positional information 515 of the capture zone 135', and the operating parameters 520 for the one or more nozzles 222. The machine learning module 250 may be configured to learn by correlating the data 500 associated with the operating state 505 of each of the one or more devices, the operating profile 510 of the workspace 105, the positional information 515 of the capture zone 135', and the operating parameters 520 for the one or more nozzles 222. In an embodiment, the machine learning module 250 may be configured to determine one or more correlations between the data 500 associated with the operating state 505 of each of the one or more devices, the operating profile 510 of the workspace 105, the positional information 515 of the required capture zone 135', and the operating parameters 520 for the one or more nozzles 222.

The machine learning module 250 may be configured to create new operating profiles 510 based on the combination of the operating state of one or more devices or any newly installed additional devices in the workspace 105. The machine learning module 250 may further be configured to define the positional information 515 of the required capture zone 135' and the operating parameters 520 for the one or more nozzles 222 for each of the new operating profiles 510, based on the determined one or more correlations. The processor 235 may then be configured to adjust the capture zone 135 according to determined new operating profiles 510 and the operating parameters of the one or more nozzles 222 in accordance with the operating parameters as determined by the machine learning module 250.

In some embodiments, the processor 235 may be configured to validate the configuration of the capture zone 135, 135', 135' and the operating parameters of the one or more nozzles 222 determined by the machine learning module 250 to ensure that the workspace 105 is protected from the airborne contaminants 120, 120', 120". To this end, the processor 235 may be configured to provide data associated with the distribution pattern of the airborne contaminants 120, 120', 120" in the workspace 105 to the machine learning module 250 on a periodic basis.

In some embodiments, the machine learning module 250 may be configured to receive a predefined training data set comprising the type of the airborne contaminants 120, 120', 120", the distribution pattern of the airborne contaminants 120, 120', 120", and the characteristics of the treatment field. The machine learning module 250 may be configured to learn by correlating the data associated with the type of the airborne contaminants 120, 120', 120", the distribution pattern of the airborne contaminants 120, 120', 120", and the characteristics of the treatment field. In an embodiment, the machine learning module 250 may be configured to determine one or more correlations between the type of the airborne contaminants 120, 120', 120", the distribution pattern of the airborne contaminants 120, 120', 120", and the characteristics of the treatment field.

The machine learning module 250 may be configured to define characteristics of the thermal fields for a particular type and a distribution pattern of the airborne contaminants 120, 120', 120" based on the determined one or more correlations. The processor 235 may then be configured to continuously adjust the characteristics of the thermal fields in real time according to the characteristics determined by the machine learning module 250.

In accordance with various embodiments, the memory 240 may include a random access memory (RAM) and read only memory (ROM). The RAM may be implemented by Synchronous Dynamic Random Access Memory (SDRAM), Dynamic Random Access Memory (DRAM), and/or any other type of random access memory device. The ROM may be implemented by a hard drive, flash memory and/or any other desired type of memory device.

Further, the processor 235 may be configured to execute the instruction stored in the memory 240, to perform the one or more predetermined operations, such as those described herein. The processor 235 may include one or more microprocessors, microcontrollers, DSPs (digital signal processors), state machines, logic circuitry, or any other device or devices that process information or signals based on operational or programming instructions. The processor 235 may be implemented using one or more controller technologies, such as Application Specific Integrated Circuit (ASIC), Reduced Instruction Set Computing (RISC) technology, Complex Instruction Set Computing (CISC) technology, etc.

The input/output unit 220 may be positioned within or remotely with respect to the workspace 105. The input/output unit 220 may include a graphical user interface (such as, a mobile phone, a tablet, a touch screen computer) or other input/output means (such as, a keyboard, a speaker, microphone, Light Emitting Diodes etc.) to communicate with the individuals (such as, the practitioner 110 and the patient) in the workspace 105. In some examples, the graphical user interface may be a mobile application or a web application associated with the system 200 and the workspace 105 in which the system 200 is employed.

Figure 6:
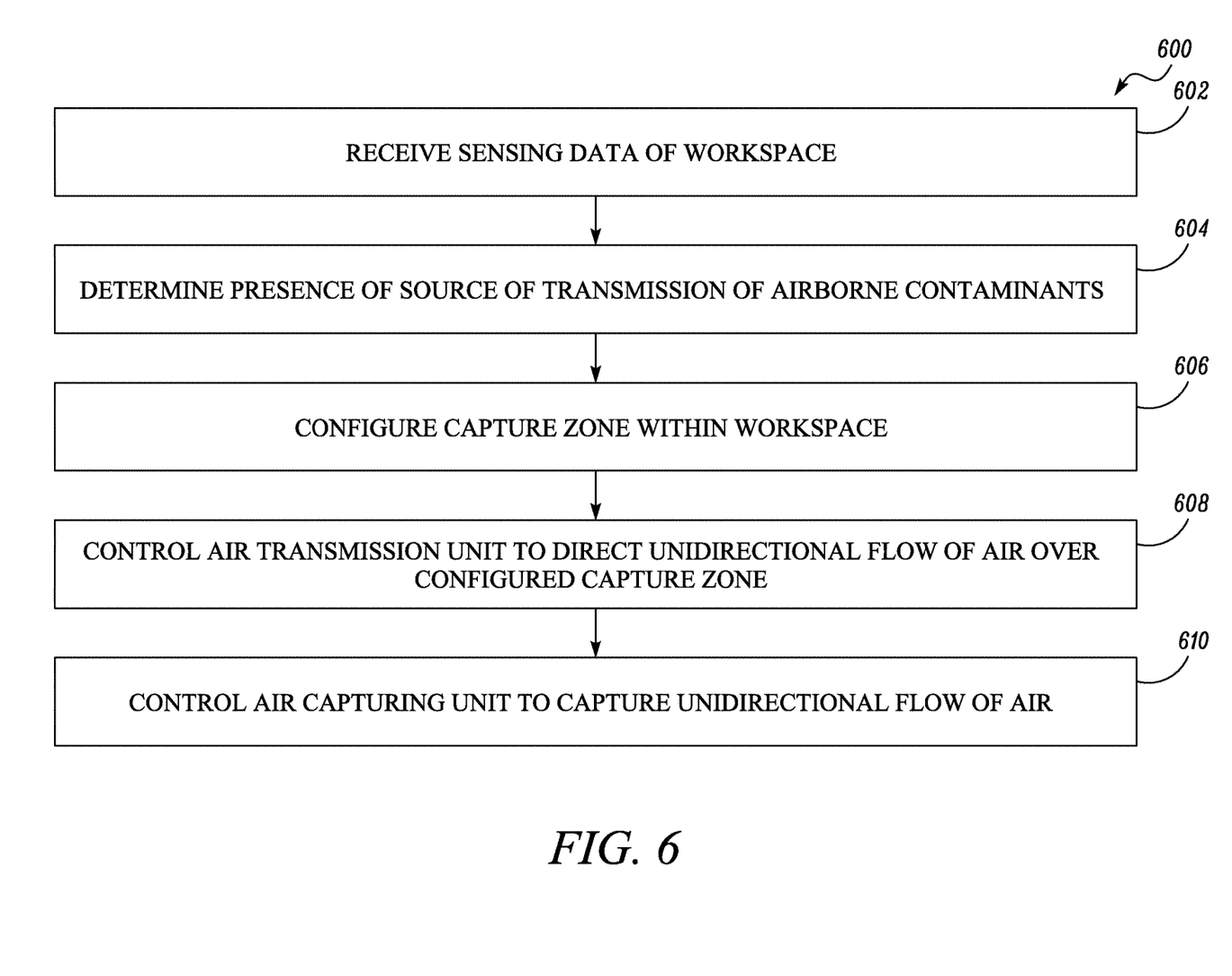
FIG. 6 illustrates an exemplary method for protecting the workspace from the airborne contaminants, in accordance with some embodiments.

FIG. 6 illustrates an exemplary method 600 for protecting the workspace 105 from the airborne contaminants 120. Initially, at Operation 602, the processor 235 receives the sensing data associated with the workspace 105 captured by the at least one sensing capturing unit 205 positioned in the workspace 105. Further, at Operation 604, the processor 235 determines presence of the at least one source 130 of transmission of the airborne contaminants 120 in the workspace 105 based on the received sensing data, such as by using machine vision techniques now known or future developed.

Further, at Operation 606, the processor 235 configures the capture zone 135 within the workspace 105 based on the determined at least one source 130 of transmission of the airborne contaminants 120 at Operation 606. In some embodiments, the processor 235 adjusts the capture zone 135 based on the operating state of one or more devices operable within the workspace 105 and/or the determined distribution pattern of the airborne contaminants 120 within the workspace 105. In an embodiment, the processor 235 first detects the presence of the one or more devices operable within the workspace 105 and determines the operating state of each of the detected one or more devices. The processor 235 then adjusts the configured capture zone 135 based on the determined operating state of each of the one or more devices operable within the workspace 105. Further, in another embodiment, the sensor unit 225 positioned within the workspace 105 detects the presence of the airborne contaminants 120" in the workspace 105 and transmits the data associated with the detected presence of the airborne contaminants 120" to the processor 235. The processor 235 then determines the distribution pattern of the airborne contaminants 120" in the workspace 105 based on the detected presence of the airborne contaminants 120". The processor 235 then further adjusts the configured capture zone 135 based on the determined distribution pattern of the airborne contaminants 120" within the workspace 105.

Further, at Operation 608, the processor 235 controls the air transmission unit 210 to direct the unidirectional flow of air 140, 140', 140" over the capture zone 135, 135', 135" thereby directing movement of the airborne contaminants 120, 120', 120" in the capture zone 135, 135', 135". In some embodiments, the processor 235 determines the intensity of the unidirectional flow of air 140, 140', 140" based at least on one of the determined operating state of the one or more devices or the determined distribution pattern of the airborne contaminants 120" present within the workspace 105 and controls the air transmission unit 210 to direct the unidirectional flow of air 140, 140', 140" with the determined intensity over the capture zone 135, 135', 135". In some additional embodiments, the processor 235 also controls the air transmission unit 210 to disperse the disinfectant over the capture zone 135, 135', 135".

At Operation 610, the processor controls an air capturing unit 215 to capture the unidirectional flow of air 140, 140', 140", along with the airborne contaminants 120, 120', 120" directed from the air transmission unit 210. In some embodiments, the processor 235 also controls the air capturing unit 215 to store air samples from the captured flow of air 140, 140', 140", along with the airborne contaminants 120, 120', 120" in the air storage container 224.

In some embodiments, the processor 235 further controls the filter unit 230 to receive the unidirectional flow of air 140, 140', 140", along with the airborne contaminants 120, 120', 120" captured by the air capturing unit 215 via the conduit 255. The processor 235 then determines the type of the airborne contaminants 120, 120', 120" captured by the air capturing unit 215 using the filter unit 230. The processor 235 further controls the filter unit 230 to disinfect the captured airborne contaminants 120, 120', 120" based on the determined type of airborne contaminants 120, 120', 120".

In some embodiments, the processor 235 further detects the malfunctioning of one or more of the air transmission unit 210, the air capturing unit 215, and the filter unit 230 and generates the alert indicative of the detected malfunctioning using the input-output unit 220. In some embodiments, the processor 235 also controls the operating state of each of the one or more devices operable within the workspace 105 when the processor 235 detects the malfunctioning of one or more of the air transmission unit, 210 the air capturing unit 215, and the filter unit 230.

The embodiments described herein provide an effective and reliable solution for protecting the workspace 105 from the airborne contaminants 120, 120', 120". The system and method described herein utilizes machine vision that automatically identifies various sources 130 of the airborne contaminants 120, 120', 120" in the workspace 105, thereby facilitating the air curtain to be formed automatically in close proximity to the sources 130 of the airborne contaminants 120, 120', 120". Moreover, the capture zone 135, 135', 135" that are suspected to be infected with the airborne contaminants 120, 120', 120" in the workspace 105 are configured and continuously adjusted based on the operating profile 510 of the workspace 105 and the distribution pattern of the airborne contaminants in the workspace 105. This ensures that all possible areas that are suspected to be infected with the airborne contaminants 120, 120', 120" are always included in the capture zone 135, 135', 135". In addition, the adjustment of the operating parameters of the one or more nozzles 222, based on the operating profile 510 of the workspace 105 and the distribution pattern of the airborne contaminants in the workspace 105, ensures that all possible airborne contaminants 120, 120', 120" are successfully trapped along with the flow of air 140, 140', 140" generated by the air transmission unit 210 and captured by the air capturing unit 215, thereby preventing airborne contaminants 120, 120', 120" emanating from the patient to enter facial area of the practitioner 110 in the workspace 105. In some embodiments, when the practitioner 110 is determined to be the source 130 of the airborne contaminants, the system and method described herein may further prevent the airborne contaminants emanating from the practitioner 110 to enter the facial area of the patient in the workspace 105. This ensures that the individuals present in the workspace 105, as well as the individuals that would use the workspace 105 in future are always safe and protected from the airborne contaminants. Moreover, the system and method described herein does not require the workers to wear any additional PPEs or garments, thereby allowing the workers to work with greater DoF.

Further, the use of machine vision and machine learning algorithms elevates the effectiveness and reliability of the system by adding a layer of intelligence that adjusts the capture zone 135, 135', 135" and the flow of air 140, 140', 140" based on a current functional environment (for example, the distribution pattern of the airborne contaminants 120, 120', 120") of the workspace 105. This ensures that the safe working environment is free from any airborne contaminants 120, 120', 120" and the required industry standards for a safe working environment are maintained at all times. Further, this adaptability and configurability make the benefits of this system and method extensible to various environments and various operating profiles applicable in the workspace 105.

Moreover, the integration of the system 200 with the specific operations' environment of the workspace 105 offers immediate additional benefits to optimize and improve the performance of the workspace environment 100. For example, when the system 200 is integrated with the chair 150, the system 200 harmonizes and regulates the operation of the ancillary one or more devices (for example: ultrasonic scalers, dental handpieces, air-water-syringes, air guns, dental drills, etc.) to further assure that the power and pressure of the ancillary one or more devices conform to the best and safest profiles to limit/manage spillover outside of the capture zone 135, 135' 135".

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, front and rear, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element preceded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. A system for protecting a workspace from airborne contaminants, the system comprising:
    at least one camera positioned within the workspace and adapted to capture a sensing data associated with the workspace;
    an air transmission unit adapted to direct a unidirectional flow of air;
    an air capturing unit adapted to receive the unidirectional flow of air directed from the air transmission unit;
    one or more devices configured to operate within the workspace;
    a memory configured to:
        store operating profiles associated with each of the one or more devices, wherein the operating profiles comprise an operating state of each of the one or more devices; and
        store a positional information of each associated capture zone for each operating profile; and
    a processor operatively coupled to the at least one camera, the air transmission unit, the air capturing unit, and the one or more devices, and the memory, the processor being configured to:
        receive the sensing data associated with the workspace from the at least one camera;
        determine presence of at least one source of transmission of the airborne contaminants in the workspace based on the received sensing data;
        define the positional information of a capture zone within the workspace based on the determined at least one source of transmission of the airborne contaminants, the capture zone being an area suspected to be infected with the airborne contaminants transmitted from the determined at least one source of transmission of the airborne contaminants in the workspace;
        determine an operating state of each of the one or more devices;

compare the operating state of each of the one or more devices to the stored operational profiles in the memory to determine the current operational profile;

change the positional information of the capture zone based on the stored positional information of each associated capture zone for the current operating profile;

determine the operating state of each of the one or more devices in the workspace;

control the air transmission unit to direct the unidirectional flow of air over the capture zone, thereby directing movement of the airborne contaminants in the capture zone; and control the air capturing unit to capture the unidirectional flow of air, along with the airborne contaminants, directed from the air transmission unit.

2. The system according to claim 1, further comprising:
at least one sensor positioned within the workspace and operatively coupled to the processor, wherein the at least one sensor is configured to detect presence and a physical area comprising positional information of the airborne contaminants in the workspace, and wherein the processor is further configured to:

determine, based on the detected presence and the area of the airborne contaminants, that the area is outside the positional information of the capture zone; and change the positional information of the capture zone to include the area with the airborne contaminants outside the positional information of the capture zone; and store the changed positional information in the memory.

3. The system according to claim 2, wherein the at least one sensor includes one or more of a thermal sensor, a vapor sensor, a chemical sensor, a visual sensor, and a biological sensor.

4. The system according to claim 1, wherein the air transmission unit comprises one or more nozzles controlled by an air nozzle controller,
wherein the memory is further configured to store data comprising operating parameters of the one or more nozzles corresponding to the operating state of the one or more devices, wherein the operating parameters comprise at least one of an angle, a height and an intensity at which the one or more nozzles operate to direct the unidirectional flow of air over the capture zone based on the positional information of the capture zone;

wherein the processor is further configured to:
determine the operating parameters of the one or more nozzles based on the data stored in memory; and
control the air nozzle controller to adjust the one or more nozzles based on the determined operating parameters.

5. The system according to claim 1, wherein the processor is further configured to control the air transmission unit to disperse disinfectant over the capture zone.

6. The system according to claim 1, further comprising:
a filter unit operatively coupled to the processor, wherein the filter unit is configured to receive the unidirectional flow of air along with the airborne contaminants captured by the air capturing unit, and
wherein the processor is further configured to
control the filter unit to disinfect the captured airborne contaminants using one or more disinfectants from a group including chemical disinfectants, ultraviolet lights, and thermal disinfection.

7. The system according to claim 1, wherein the air capturing unit includes an air storage container, and wherein the processor is further configured to control the air capturing unit to store air samples from the captured flow of air along with the airborne contaminants in the air storage container.

8. The system according to claim 6, further comprising:
an input-output unit positioned within the workspace and operatively coupled to the processor,
wherein the processor is further configured to:
detect a malfunctioning of one or more of the air transmission unit, the air capturing unit, and the filter unit, and
generate, using the input-output unit, an alert indicative of the detected malfunctioning.

9. The system according to claim 8, wherein the processor is further configured to:
control an operating state of the one or more devices when the processor detects the malfunctioning of one or more of the air transmission unit, the air capturing unit, and the filter unit.

* * * * *